United States Patent
Furuta et al.

[11] Patent Number: 5,968,833
[45] Date of Patent: Oct. 19, 1999

[54] TEST PIECE AND METHOD OF USE FOR MEASURING MAGNESIUM IN BIOLOGICAL FLUID

[75] Inventors: Hitoshi Furuta; Shinzo Yoshida; Junji Yoshioka; Hisashi Ashida, all of Kyoto, Japan

[73] Assignee: Kyoto Daiichi Kagaku Co., Ltd., Kyoto, Japan

[21] Appl. No.: 08/827,247

[22] Filed: Mar. 28, 1997

[30] Foreign Application Priority Data

Mar. 29, 1996 [JP] Japan ..................................... 8-112908

[51] Int. Cl.⁶ ...................................................... G01N 33/48
[52] U.S. Cl. ........................... 436/79; 436/164; 436/166; 436/169; 422/56; 422/61
[58] Field of Search ................... 422/56, 58, 61; 436/79, 164, 166, 169, 170, 174

[56] References Cited

U.S. PATENT DOCUMENTS

| | | | |
|---|---|---|---|
| 3,754,864 | 8/1973 | Gindler | 23/230 |
| 3,992,158 | 11/1976 | Przybylowicz et al. | 422/58 |
| 5,124,129 | 6/1992 | Riccitelli et al. | 422/56 |
| 5,397,710 | 3/1995 | Steinman | 436/79 |
| 5,618,684 | 4/1997 | Nonobe et al. | 436/15 |

FOREIGN PATENT DOCUMENTS

| | | |
|---|---|---|
| 0044775 | 1/1982 | European Pat. Off. . |
| 0254202 | 1/1988 | European Pat. Off. . |
| 62-64950 | 3/1987 | Japan . |

OTHER PUBLICATIONS

Abstract–Journal, Yamane, Takeshi; Goto, Eiichi, Fac. Educ., Yamanashi Univ., Kofu, 400, Japan, Talanta (1991), 38(2), 139–43, Coden: TLNTA2; ISSN; 0039–9140, 1991.

*Primary Examiner*—Lyle A. Alexander
*Attorney, Agent, or Firm*—Sughrue, Mion, Zinn, Macpeak & Seas, PLLC

[57] ABSTRACT

A dry test piece for measuring a magnesium concentration in a biological fluid, which comprises the following reagent components (i) to (iii): (i) o-cresolphthalein complexon; (ii) O,O'-bis(2-aminophenyl)ethylene glycol-N,N,N',N'-tetraacetic acid; and (iii) a pH buffer agent of pH 8.5 to 11.0.

13 Claims, 2 Drawing Sheets

TEST PIECE AND METHOD OF USE FOR MEASURING MAGNESIUM IN BIOLOGICAL FLUID

FIELD OF THE INVENTION

The present invention relates to a dry test piece for easily measuring the magnesium concentration of a biological fluid, particularly a body fluid such as serum and plasma.

BACKGROUND OF THE INVENTION

Magnesium is a bivalent metal having the largest content in the living body next to calcium and is an important essential element which is deeply concerned in various enzyme reactions in vivo. The magnesium concentration of serum and plasma changes in competition with the calcium concentration and the changes are observed at the time of central nervous system or heart insufficiency, renal insufficiency, acute pancreatitis and the like, so that the measurement of magnesium is one of the important clinical diagnostics items.

Various methods are known for the colorimetric determination and measurement of magnesium concentration in liquid samples using a bivalent metal chelating indicator. The chelating indicator most frequently used is Xylidyl Blue I. According to Dojin Kagaku Catalog 19th edition (published on May 31, 1994), the calorimetric determination of magnesium can also be effected using Eriochrome Black T, Calcichrome, Carboxyarsenazo, Calmagite, Chlorophosphonazo III, Methyl Thymol Blue, o-Cresolphthalein Complexon, SPANS, Xylenol Orange and the like.

When the calorimetric determination of magnesium in biological samples is carried out using these chelating indicators, it is necessary to add a calcium masking agent in order to avoid the interference of coexisting calcium, independent of the indicators. Examples of the masking agent selective for calcium in the coexistence of magnesium and calcium include O,O'-bis(2-aminomethyl)ethylene glycol-N,N,N',N'-tetraacetic acid (hereinafter often referred to as "GEDTA"), trans-1,2-diaminocyclohexane-N,N,N',N'-tetraacetic acid (hereinafter often referred to as "CyDTA"), and O,O'-bis(2-aminophenyl)ethylene glycol-N,N,N',N'-tetraacetic acid (hereinafter often referred to as "BAPTA").

Addition of triethanolamine or a cyanide compound is also known as a method for masking other heavy metals such as iron, copper and zinc.

Preparation of a reagent composition for use in the measurement of magnesium by these combinations is now an idea which can easily be deduced by those skilled in the art, and a large number of reagent compositions for use in the measurement of magnesium have been devised and put into practical use. For example, a combination of Xylidyl Blue I with GEDTA is used most commonly, and many reagent kits thereof are now on the market. For example, JP-A-4-120464 discloses a combination of Chlorophosphonazo III with GEDTA or BAPTA (the term "JP-A" as used herein means an "unexamined published Japanese patent application"), EP-A-597900 discloses a combination of Arsenazo I with GEDTA or BAPTA, and JP-A-5-11908 discloses a method in which a formazan derivative is used.

The combination disclosed in U.S. Pat. No. 5,397,710 relates to a dry test piece for total blood use having a blood cell separating function. It uses Eriochrome Black T, Calmagite, Magon, Chlorophosphonazo III, Hydroxynaphthol Blue, Arsenazo I, SPANS or the like as the indicator, and GEDTA as the masking agent.

Of the chelating indicators used in the prior art, every indicator excluding formazan derivatives has an allylazo structure as the chelate action functioning portion and a naphthol structure as the pigment moiety.

Now, when a liquid sample is analyzed using a dry reagent, the sample is mostly un-diluted serum, plasma, urine or the like, and the substance to be measured is contained in a fairly high concentration in many cases. Magnesium is not exceptional, and the concentration in human serum or plasma is normally 1.8 to 2.0 mg/dl and sometimes reaches 5.0 to 6.0 mg/dl in abnormal cases. The test piece must have a capacity to measure such abnormal values.

That is, when a dry test piece for use in the measurement of magnesium is prepared using a metal chelating indicator, the chelating indicator in the reagent must be included in advance in a necessary and sufficient amount for the magnesium concentration in samples (the upper limit concentration of the intended measuring range including abnormal values). However, when the chelating indicator is added in such a necessary and sufficient amount, a significantly high level of coloring is observed even under free and un-developed conditions before forming a complex body with magnesium. In other words, these methods have a disadvantage in that the measuring accuracy of a sample having a low magnesium concentration becomes poor due to the high initial background value.

Since the magnesium concentration in biological fluid, such as serum and plasma, is controlled by considerably strong homeostasis, the normal value is limited to an extremely narrow range. Consequently, since it is important in the diagnosis of diseases to detect a value slightly deviated from the narrow range, the poor measuring accuracy is a fatal disadvantage.

Additionally, when the inventors of the present invention have attempted to prepare various dry test pieces for measuring the magnesium concentration using dry-processing thinkable combinations of the prior art magnesium chelating indicators and calcium masking agents, it was found that the interference of calcium could not be avoided in most of the combinations including the prior art combinations.

Also, many of the thus obtained dry test pieces showed a poor storage stability even under cold storage conditions (4 to 8° C.).

SUMMARY OF THE INVENTION

An object of the present invention is to provide a dry test piece for measuring a magnesium concentration which shows low background value, has excellent measuring accuracy within the entire measuring range, is not interfered by coexisting calcium, has an excellent storage stability and can be used easily and simply.

This and other objects of the present invention have been attained by a dry test piece for measuring a magnesium concentration in a biological fluid, which comprises the following reagent components (i) to (iii):

(i) o-cresolphthalein complexon (hereinafter often referred to as "OCPC");

(ii) O,O'-bis(2-aminophenyl)ethylene glycol-N,N,N',N'-tetraacetic acid (BAPTA); and (iii) a pH buffer agent of pH 8.5 to 11.0.

The dry test piece may further contain an ionic detergent as reagent component (iv).

Moreover, this and other objects of the present invention have been attained by the above dry test piece, wherein the dry test piece comprises a water impermeable support having provided thereon a detecting region;

wherein the detecting region comprises a sample retaining layer comprising a water insoluble porous material, and a binder layer comprising a water soluble polymer, and wherein the reagent components are present in at least one of the sample retaining layer and the binder layer.

DETAILED DESCRIPTION OF THE INVENTION

Figure 1:
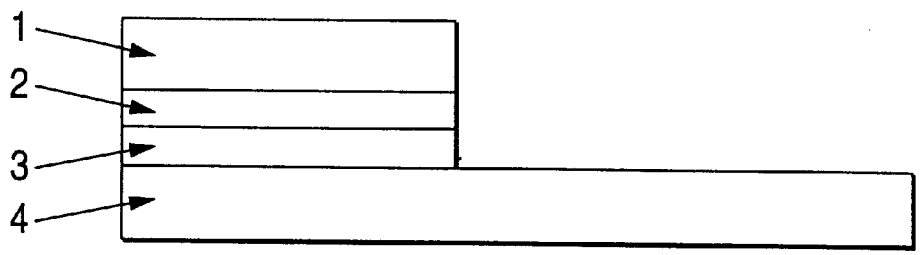
FIG. 1 is a sectional view of the detecting region and the surrounding area of the test piece according to the present invention, in which reference numeral 1 designates sample retaining layer, reference numeral 2 designates binder layer, reference numeral 3 designates water impermeable support, and reference numeral 4 designates base film.

Although a technique to measure calcium or magnesium using OCPC is an already known method, application of the combination of OCPC and BAPTA to the specific measurement of magnesium is a technique which cannot be found in the prior art. The present inventors have found that the interference of calcium can be avoided completely without reducing sensitivity of the magnesium measurement when a test piece is prepared using OCPC together with BAPTA as a calcium masking agent.

Since OCPC and BAPTA are both chelating agents of bivalent metals, they form chelate complex with both magnesium and calcium. However, OCPC has much larger chelation stability constant for magnesium than BAPTA has, and BAPTA has much larger chelation stability constant for calcium than OCPC has. The present invention has been accomplished by applying this principle through a specific combination of OCPC and BAPTA.

Since dry test pieces are measured mainly by optical method, it is preferable as a matter of course that the background value at the detecting area is low. The test piece comprising OCPC in the present invention has an extremely low background value, and it has light pink color before the reaction even when it is added in a large amount in preparing a test piece. Consequently, a test piece having high accuracy can be completed.

The sensitivity of magnesium measurement using OCPC becomes high as the pH value becomes high (as the alkalinity becomes strong). Also, OCPC develops color when it becomes alkaline even in the absence of magnesium. The processing into dry test pieces has not been put into practical use because of a problem in that the background value becomes high when adjusted to a strongly alkaline side in order to increase the sensitivity which, on the contrary, is reduced when adjusted to neutral side. In the present invention, however, it was able to obtain a test piece having low background without reducing the sensitivity by using a pH buffer agent capable of adjusting the reaction system to pH 8.5 to 11.0. This can simultaneously inhibit reduction of the pH value caused by carbon dioxide contained in the atmosphere during the preparation.

It is known also that, when magnesium in biological fluids, such as serum or plasma samples, is measured by general chelate reaction systems including OCPC, the measurement is interfered by proteins, particularly albumin, in the samples. This phenomenon due to the nature of magnesium to be adsorbed by albumin does not cause practical problems, because the portion of magnesium which is adsorbed by albumin in serum or plasma has an almost constant ratio of about 30% so that it can be canceled by a simple numerical processing.

However, such an interference cannot be ignored in some cases when a sample has an extremely low or high albumin level. The present invention has rendered possible prevention and avoidance of dispersion among a plurality of samples to be tested including samples having extremely low or high albumin level, by adding to the reaction system an ionic detergent having a protein denaturation function.

According to the test piece in the present invention, a concentration of magnesium in serum and plasma can be measured accurately within a few minutes, so that it is markedly useful in clinical diagnostics. Also, being a dry type test piece, it can be handled markedly simply and easily.

It is necessary to add a chelating indicator in a high concentration, because measurement at around the upper limit of measuring range becomes impossible when the concentration is not sufficient. However, the addition in too excess amount causes a high background value. Since OCPC does not cause a high background even when added in a high concentration in comparison with other chelating indicators, it can maintain the measuring accuracy. It may be added preferably within the range of from 0.05 to 0.3%, more preferably within the range of from 0.07 to 0.15%, as % by dry weight of the detecting region. The dry weight of the detecting region means the dry weight of the detecting region containing the reagent components, the sample retaining layer and the binding layer.

BAPTA may be added in a sufficient amount for the concentration of calcium to be expected. In the measurement of serum or plasma sample, it may be preferably from 0.3 to 5.0%, more preferably from 0.5 to 1.5%, by dry weight of the detecting region.

The pH buffer agent can be optionally selected from known buffer agents conventionally used in such a type of test pieces, with the proviso that it can be used within the pH range of from 8.5 to 11.0 and the components do not evaporate when dried. Examples thereof include a boric acid-sodium hydroxide buffer, a sodium bicarbonate-sodium carbonate buffer, a glycine-sodium hydroxide buffer, a CHES buffer, and a CAPSO buffer. Although the measurement of magnesium can be effected sufficiently when the pH value is within the range of from 8.5 to 11.0, the pH range may be preferably from 9.5 to 10.0. The buffer may be used in a concentration of preferably from 0.3 to 5.0%, more preferably from 1.0 to 3.0%, by dry weight of the detecting region.

The water impermeable support for use in the dry test piece of the present invention is a surface-roughened white film comprising a plastic material such as polyethylene terephthalate, polystyrene or the like, having a thickness of from 50 μm to 1 mm, preferably from 100 μm to 300 μm.

The detecting region comprises a water soluble binder layer and a sample retaining layer comprising a water insoluble porous material laminated on the water impermeable support.

When the binder layer contains reagent components, the binder layer is prepared by uniformly coating the reagent components on the support at the time of the production of the detecting region, thereby serving as an adhesive when the sample retaining layer is laminated and also as a layer to maintain the developed color uniformly at the time of the measurement.

Because the samples to be measured are biological fluids such as serum, plasma and the like, a water soluble polymer is used as the material of the binder layer, which can be optionally selected with the proviso that it contains substantially no magnesium and calcium. Examples thereof include polyacrylamide and polyvinyl pyrrolidone. These materials may be added in such a manner that the coating solution has an appropriate viscosity. The concentration in the coating solution is 4 to 6% in the case of polyacrylamide or 10 to 15% in the case of polyvinyl pyrrolidone. The concentration of the polymer for use in the adjustment of appropriate viscosity greatly varies within the range of from 0.5 to 20%, preferably from 5.0 to 10% (after drying) depending on the kind. The reagent components may not be included in the above binder layer and be included only in the sample retaining layer described below in an impregnated form.

The sample retaining layer is used for uniformly developing a sample on the reagent surface at the time of the applying, retaining the sample while the reaction with the reagents and making the reagents after the reaction into optically detectable conditions. As the water insoluble porous material for use in the sample retaining layer, a filter or membrane filter comprising cellulose, a cellulose derivative or glass fibers or a textile material comprising natural or chemical fibers may be used if necessary after washing and drying. In a preferred example, a wet or dry textile material such as a piece of cloth is pressed and laminated on the binder layer. The % by weight of the sample retaining layer when dried occupies 65 to 95%, preferably 75 to 85%, of the detecting region.

The coating solution of the binder layer is coated uniformly on the water impermeable support within the range of thickness from 50 to 300 μm, preferably from 100 to 200 μm, by any known coating method as disclosed, for example, in U.S. Pat. Nos. 3,992,158, 4,042,335, and 4,258,001. The thus coated binder layer is dried by blowing hot air of 40 to 60° C.

When the sample retaining layer is laminated on the binder layer, the reagent components in the binder layer may sometimes be transferred into the sample retaining layer together with the polymer, so that both layers may not be separated clearly from each other in some cases in the detecting region defined in the present invention.

In any case, both of the sample retaining layer and binder layer in the detecting region optionally contain the combination of OCPC and BAPTA and the pH buffer agent for use in the present invention.

When a dry reagent for measuring a magnesium concentration is prepared according to the present invention, a test piece having high performance is obtained by further adding an ionic detergent which denatures protein for avoiding the influence of albumin in serum or plasma. Examples thereof include sodium dodecyl sulfate as an anionic detergent and tetradecyltrimethylammonium bromide as a cationic detergent, though it will be apparent to those skilled in the art that any other compound can be used with the proviso that it is an ionic detergent having similar function. The concentration of the ionic detergent is preferably from 0.3 to 20.0%, more preferably from 5.0 to 15.0%, by dry weight of the detecting region.

It is possible to add other components to the detecting region, such as a cyanide compound for masking of metals other than calcium and a stabilizer of the metal chelating indicator, but these additional components are not particularly required in the dry reagent composition of the present invention.

The original sheet of the thus obtained detecting region of the dry test piece of the present invention is cut into a small piece and adhered to a base film which can be held with fingers, thereby obtaining a test piece for use in the measurement of magnesium. The sectional view is shown in FIG. 1 (1: sample retaining layer; 2: binder layer; 3: water impermeable support; 4: base film which can be held with fingers). Since base film 4 is merely a handle, it is not an essential composing element of the present invention. The test piece of the present invention having no base film can be obtained by cutting the original sheet of detecting region into a strip.

An appropriate amount of a liquid sample is applied on the detecting region of the test piece, and the reflectance after completion of the reaction is measured from the detecting region side or from the support side (when measured from the support side, it is essential that materials of the support and handle are light transmittable). The reflectance is measured at a wavelength close to the absorption peak of the chelate complex of OCPC and magnesium, preferably at 565 to 575 nm.

High accuracy measurement can be made by controlling the applying volume of liquid sample, reaction temperature and reaction time at constant levels.

The present invention will now be illustrated in greater detail with reference to Examples, but it should be understood that the invention is not construed as being limited thereto.

EXAMPLE

Preparation of Coating Solution of Binder Layer (Formulation)

| | |
|---|---|
| o-Cresolphthalein Complexon (Dojin Kagaku) | 1.50 mmol/λ |
| O,O'-Bis(2-aminophenyl)ethylene glycol-N,N,N',N'-tetraacetic acid tetra salt (Dojin Kagaku) | 16 mmol/λ |
| Sodium borate buffer (pH 9.5) (Wako Pure Chemical) | 300 mmol/λ |
| Sodium dodecyl sulfate (Wako Pure Chemical) | 10.0% (w/w) |
| 10% Acrylamide (polymer) (Nakalai Tesque) | 5.0% (w/w) |

Preparation of the Original Sheet of Detecting Region

The thus prepared solution was coated in a thickness of 120 μm (wet state) on a white polyethylene terephthalate film having a thickness of 200 μm and dried by blowing hot air of 45° C. for 15 minutes.

To this was pressure-adhered a piece of a textile material of about 250 μm in thickness which had been uniformly wetted with aqueous solution of 0.1% Triton X-100 (Nakalai Tesque), subsequently drying with a blow of hot air of 45° C. for 15 minutes.

The original sheet of detecting region after the drying contains the following components per 1 $m^2$.

| | |
|---|---|
| o-Cresolphthalein Complexon | 94.3 mg (0.09%) |
| O,O'-Bis(2-aminophenyl)ethylene glycol-N,N,N',N'-tetraacetic acid tetra potassium salt | 1.21 g (0.08%) |
| Boric acid | 2.23 g (1.80%) |
| Sodium hydroxide | 0.74 g (0.78%) |
| Sodium dodecyl sulfate | 1.20 g (10.85%) |
| Acrylamide | 6.0 g (0.71%) |
| Triton X-100 | 143 mg (0.03%) |
| Textile material | 102 g (84.86%) |

The values in the parentheses represent % by dry weight of the detecting region.

Preparation of Test Piece

The thus obtained original sheet of detecting region was cut into a small piece of 5 mm×7 mm and made into a test piece by adhering it on the tip of a white polyethylene terephthalate base film to be used as a handle in a strip shape (5 mm×80 mm) having a thickness of 0.5 mm, using a pressure sensitive adhesive double coated tape. A sectional view of the detecting region and the surrounding area at this stage is shown in FIG. 1.

Measuring Procedure

A desk-top reflectance measuring apparatus, SPOTCHEM® SP-4410, manufactured by Kyoto Dai-ichi Kagaku Co., Ltd. was used as the measuring apparatus. The test piece was put on the apparatus table which was controlled at 37° C., 5.0 µl of a serum sample was applied on the test piece and then reflectance (R) at a wavelength of 575 nm was measured after a predetermined period of time. The reflectance (R) was converted into K/S value by the Kubelka-Munk formula*.

* Kubelka-Munk formula: $K/S=(1-R)^2/2R$

Figure 2:
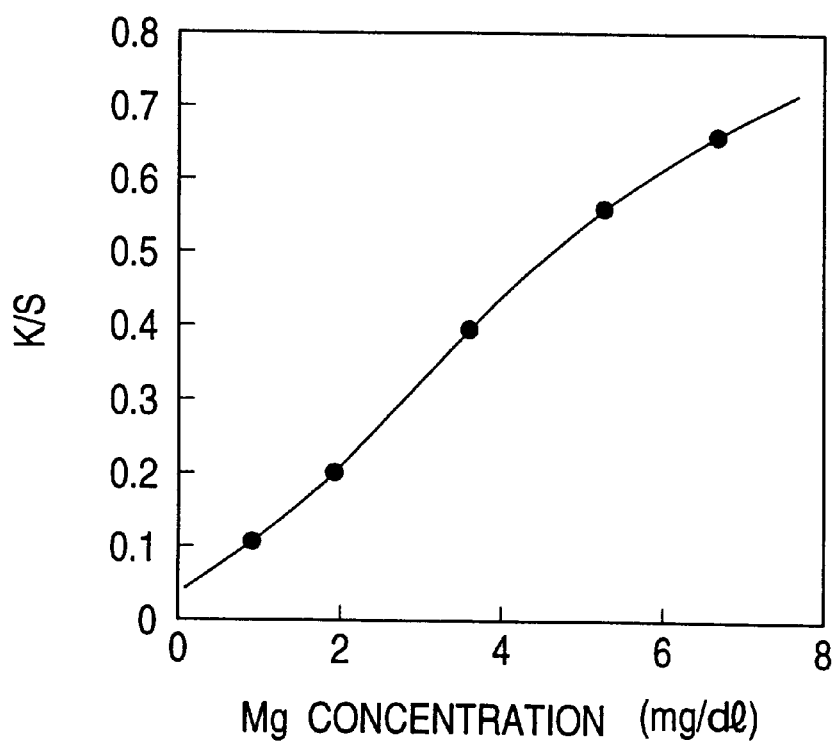
FIG. 2 is a calibration curve for optical measurement of magnesium using the test piece according to the present invention.

A calibration curve of "K/S value-magnesium concentration" was prepared in advance by measuring samples of known concentrations. The calibration curve is shown in FIG. 2. Using the curve, magnesium concentration in each sample was calculated.

Evaluation of Reproducibility Within-Run

In order to evaluate within-run reproducibility of the test piece of the present invention, three serum samples of low concentration (sample 1), normal concentration (sample 2) and high concentration (sample 3) were continuously measured 12 times for each. As shown in Table 1, coefficient of variation (CV) was 3% or less in each sample.

TABLE 1

| | Sample 1 | Sample 2 | Sample 3 |
|---|---|---|---|
| Mg (mg/dl) | 1.52 | 2.05 | 5.09 |
| 1 | 1.5 | 2.0 | 5.1 |
| 2 | 1.5 | 2.1 | 5.2 |
| 3 | 1.5 | 2.0 | 5.1 |
| 4 | 1.5 | 2.1 | 5.1 |
| 5 | 1.6 | 2.1 | 5.0 |
| 6 | 1.5 | 2.1 | 5.0 |
| 7 | 1.5 | 2.0 | 5.1 |
| 8 | 1.5 | 2.1 | 5.0 |
| 9 | 1.5 | 2.1 | 5.1 |
| 10 | 1.5 | 2.2 | 5.1 |
| 11 | 1.5 | 2.1 | 5.2 |
| 12 | 1.4 | 2.1 | 5.0 |
| AVG (mg/dl) | 1.50 | 2.08 | 5.08 |
| STD (mg/dl) | 0.043 | 0.058 | 0.072 |
| CV (%) | 2.84 | 2.77 | 1.41 |

Interference of Coexisting Calcium

Figure 3:
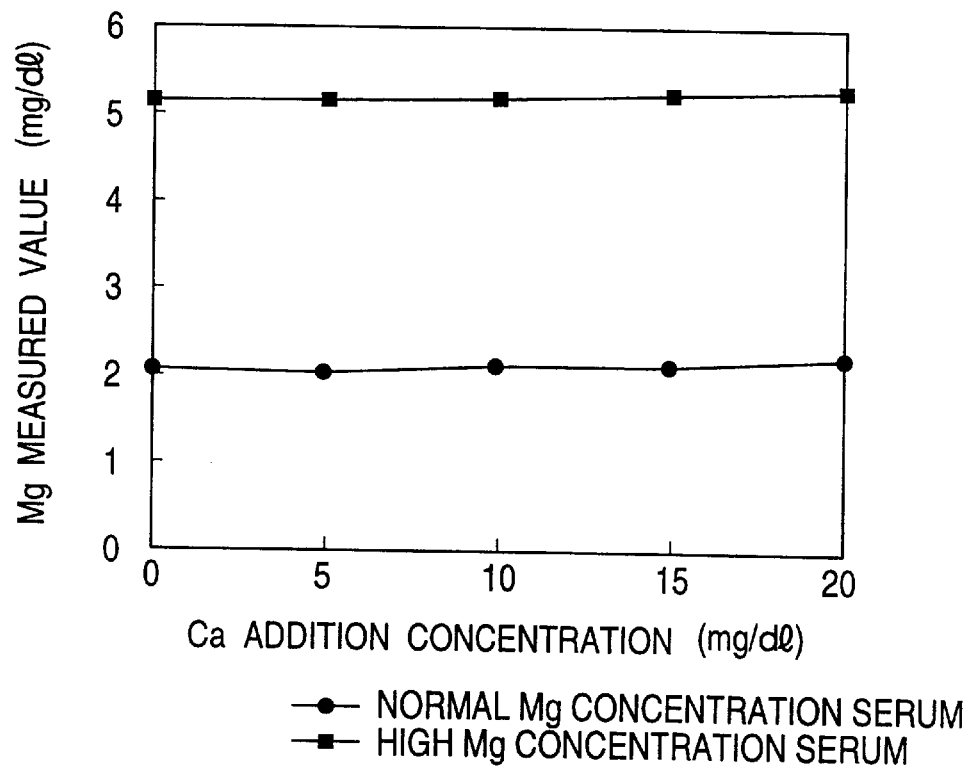
FIG. 3 shows the interference of coexisting calcium on the measurement of magnesium using the test piece according to the present invention.

In order to confirm resistance of the test piece of the present invention against interference of calcium, various amounts of calcium was added to serum samples of normal and high magnesium concentrations, and the influence upon the measured value of magnesium was examined. As shown in FIG. 3, the measurement is completely free from the interference of calcium up to 20 mg/dl.

Confirmation of Storage Stability

Figure 4:
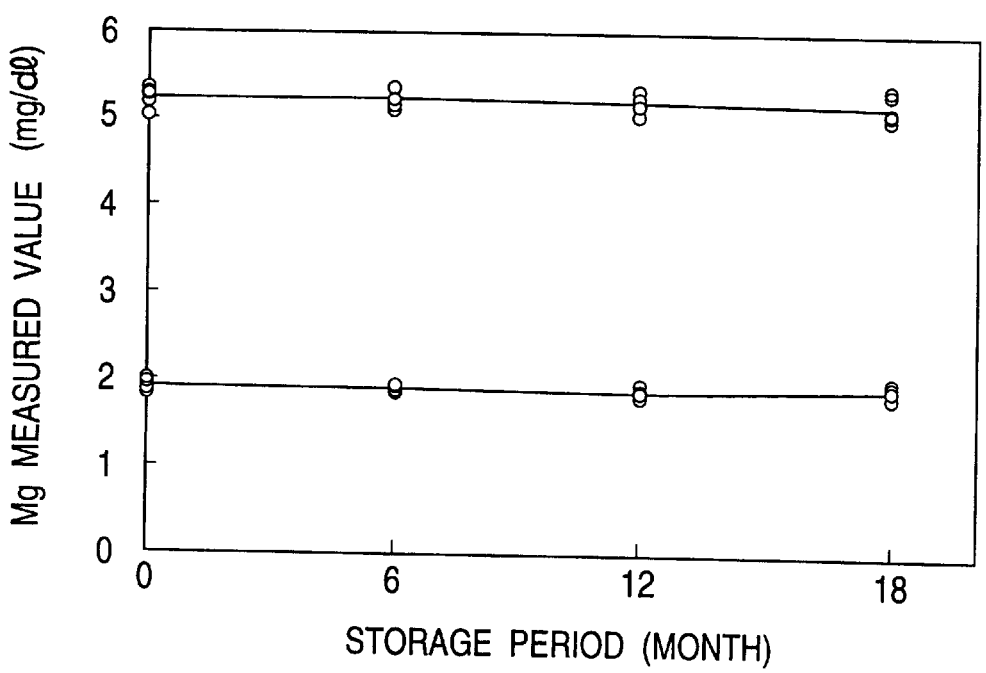
FIG. 4 shows the storage stability of the test piece according to the present invention.

Test pieces of the present invention were sealed in a glass bottle together with a desiccant and preserved under a refrigeration condition (4° C.) to examine the stability. After the lapse of period shown in FIG. 4 (initial stage and 6, 12 and 18 months), serum samples of normal and high magnesium concentrations were measured each for 6 times using the thus preserved test pieces. As shown in FIG. 4, changes in the sensitivity were hardly observed which confirmed that the test piece of the present invention is markedly stable.

Thus, as described above in detail, according to the present invention, a dry test piece for use in the quick and dry measurement of magnesium in serum and plasma sample can be obtained which has excellent measuring accuracy within the entire measuring range, shows a low background value, is not interfered by coexisting calcium, has a high storage stability and can be handled simply and easily.

While the invention has been described in detail and with reference to specific examples thereof, it will be apparent to one skilled in the art that various changes and modifications can be made therein without departing from the spirit and scope thereof.

This application is based on application No. Hei 8-112908 filed in Japan, the content of which is incorporated hereinto by reference.

What is claimed is:

1. A dry test piece for measuring a magnesium concentration in a biological fluid, comprising a water impermeable support having provided thereon a detecting region, wherein said detecting region contains reagent components comprising o-cresolphthalein complexon, O,O'-bis(2-aminophenyl) ethylene glycol-N,N,N',N'-tetraacetic acid, and a pH buffer agent of pH 8.5 to 11.0.

2. The test piece as claimed in claim 1, which further contains an ionic detergent.

3. The test piece as claimed in claim 2, wherein said ionic detergent is selected from the group consisting of sodium dodecyl sulfate and tetradecyltrimethylammonium bromide.

4. The dry test piece as claimed in claim 1,
    wherein the detecting region comprises a sample retaining layer comprising a water insoluble porous material, and a binder layer comprising a water soluble polymer; and
    wherein the reagent components are present in at least one of the sample retaining layer and the binder layer.

5. The test piece as claimed in claim 4, wherein said dry test piece further contains an ionic detergent as a reagent component.

6. The test piece as claimed in claim 5, wherein the ionic detergent is selected from the group consisting of sodium dodecyl sulfate and tetradecyltrimethylammonium bromide.

7. The test piece as claimed in claim 2, wherein said o-cresolphthalein complexon is present in an amount of from 0.05 to 0.3 wt %, said O,O'-bis(2-aminophenyl) ethylene glycol-N,N,N',N'-tetraacetic acid is present in an amount of from 0.3 to 5.0 wt %, said pH buffer agent of pH 8.5 to 11.0 is present in an amount of from 0.3 to 50. wt %, said ionic detergent is present in an amount of from 0.3 to 20.0 wt %, said water in soluble polymer is present in an amount of from 0.5 to 20 wt %, and said water insoluble porous material is present in an amount of from 65 to 95 wt %, wherein each wt % is a % by dry weight of the detecting region.

8. A method for measuring magnesium concentration while masking calcium comprising the steps of:

obtaining a biological sample;

applying said biological sample to a dry test piece comprising a water impermeable support having provided thereon a detecting region, wherein said detecting region contains reagent components comprising o-cresolphthalein complexon, O,O'-bis(2-aminophenyl)ethylene glycol-N,N,N,'N'-tetraacetic acid, and a pH buffer agent of pH 8.5 to 11.0;

allowing said biological sample to react with said reagent components in said detecting region; and measuring the reflectance after completion of the reaction.

9. The method for measuring magnesium concentration while masking calcium as claimed in claim 8, wherein an ionic detergent having a protein denaturation function is added to the reaction system.

10. The method for measuring magnesium concentration while masking calcium as claimed in claim 9, wherein said ionic detergent is selected from the group consisting of sodium dodecyl sulfate and tetradecyltrimethylammonium bromide.

11. The method for measuring magnesium concentration while masking calcium as claimed in claim 8, wherein a chelating indicator is added to the reaction system.

12. The method for measuring magnesium concentration while masking calcium as claimed in claim 8, wherein said chelating indicator is added in the range of from 0.05 to 0.3%, as by dry weight of the detecting region.

13. The method for measuring magnesium concentration while masking calcium as claimed in claim 8, wherein said reflectance is measured at a wavelength of from 565 to 575 nm.

* * * * *